United States Patent
Hoglund et al.

(10) Patent No.: US 7,839,266 B2
(45) Date of Patent: Nov. 23, 2010

(54) SYSTEM AND METHOD FOR MANAGING POINT OF CARE ASSIGNMENTS

(75) Inventors: David H. Hoglund, Lake Tahoe, NV (US); Brian McAlpine, Windham, NH (US); Eric Gentry, Godfrey, IL (US); Christopher Almy, Stow, MA (US)

(73) Assignee: LinkSense, Inc., Windham, NH (US)

( * ) Notice: Subject to any disclaimer, the term of this patent is extended or adjusted under 35 U.S.C. 154(b) by 861 days.

(21) Appl. No.: 11/748,807

(22) Filed: May 15, 2007

(65) Prior Publication Data

US 2007/0267475 A1 Nov. 22, 2007

Related U.S. Application Data

(60) Provisional application No. 60/800,295, filed on May 15, 2006.

(51) Int. Cl.
*G08B 5/22* (2006.01)

(52) U.S. Cl. ............. 340/286.07; 340/505; 340/538.15; 340/539.1; 340/539.11; 340/539.12; 340/539.23; 340/10.1; 340/286.08; 340/573.1

(58) Field of Classification Search ................. 340/505, 340/538.15, 539.1, 539.11, 539.12, 539.13, 340/539.21, 539.23, 573.4, 10.1, 286.08, 340/573.1, 286.07
See application file for complete search history.

(56) References Cited

U.S. PATENT DOCUMENTS 4,835,372 A    5/1989    Gombrich et al. ........... 235/375

(Continued)

OTHER PUBLICATIONS

Valli, C., et al. "An Investigation into Long Range Detection of Passive UHF RFID Tags," *Abstract*, 2005, pp. 1-3.

(Continued)

*Primary Examiner*—Daryl Pope
(74) *Attorney, Agent, or Firm*—Sunstein Kann Murphy & Timbers LLP

(57) ABSTRACT

A portable, battery-powered per-patient device automatically detects and logs patient encounters with items, such as medical equipment, drug containers, caregivers, visitors and other patients, in a healthcare facility. A separate per-patient device is assigned to each patient in the facility. The per-patient device is intended to remain with the patient during the patient's stay. The device may be attached to the patient's bed, wheelchair, walker or the like. If the patient is ambulatory, the patient may carry the device. RF-ID or other suitable tags are attached to items that a patient may encounter. Each per-patient device automatically detects and logs RF-ID-tagged items, including the patient, that come within a range of the device. The device also detects and longs when an item is no longer within range of the device, such as because a caregiver leaves the patient's room or a medical device is removed from the patient's room. The per-patient device also detects and logs when an item is reunited with a patient. Information, such as a time and date on which an RF-ID tag is detected or ceases to be detected, may be included in the log. The logged information may be used to obtain status or location information about the items. In addition, if an item or a patient is found to be infected, all the people or items that encountered the item or patient can be listed by querying the log.

83 Claims, 6 Drawing Sheets

U.S. PATENT DOCUMENTS

| | | | |
|---|---|---|---|
| 4,857,716 A | 8/1989 | Gombrich et al. | 235/462 |
| 5,153,584 A * | 10/1992 | Engira | 340/870.18 |
| 5,732,401 A * | 3/1998 | Conway | 705/29 |
| 6,600,421 B2 * | 7/2003 | Freeman | 340/573.1 |
| 7,242,306 B2 * | 7/2007 | Wildman et al. | 340/573.1 |
| 2002/0044059 A1 | 4/2002 | Reeder et al. | 340/573.1 |
| 2003/0025604 A1 * | 2/2003 | Freeman | 340/573.1 |
| 2003/0140928 A1 | 7/2003 | Bui et al. | 128/898 |
| 2003/0174049 A1 | 9/2003 | Beigel et al. | 340/10.42 |
| 2004/0019464 A1 | 1/2004 | Martucci et al. | 702/189 |
| 2004/0167465 A1 | 8/2004 | Mihai et al. | 604/67 |
| 2005/0086072 A1 | 4/2005 | Fox, Jr. et al. | 705/2 |
| 2005/0102167 A1 | 5/2005 | Kapoor | 705/3 |
| 2005/0108057 A1 | 5/2005 | Cohen et al. | 705/3 |
| 2005/0110640 A1 | 5/2005 | Chung | 340/572.1 |
| 2005/0251418 A1 | 11/2005 | Fox, Jr. et al. | 705/2 |
| 2006/0089539 A1 | 4/2006 | Miodownik et al. | 600/300 |
| 2006/0155584 A1 | 7/2006 | Aggarwal | 705/3 |
| 2006/0242293 A1 | 10/2006 | Russ | 709/224 |
| 2006/0277202 A1 | 12/2006 | Dempsey | 707/10 |
| 2007/0008138 A1 | 1/2007 | Mosher et al. | 340/572.4 |

OTHER PUBLICATIONS

"RFID Smart Cards Gain Ground," RFID Journal, RFID (Radio Frequency Identification) Technology News and Features, http://www.rfidjournal.com/article/articlereview/374/1/1/ Apr. 9, 2003, pp. 1-3.

ElAmin, A. "Radar Reader Spots RFID Tag Location at a Distance," Food Productiondaily.com, http://www.foodproductiondaily.com/news/printNewsBis.asp?id=63448 May 7, 2007, pp. 1-2.

"Identifying and Locating Low Cost RFID Transporters," RFID-Radar—A New Identification Technology, http://www.rfid-radar.com, May 15, 2007, pp. 1-11.

* cited by examiner

SYSTEM AND METHOD FOR MANAGING POINT OF CARE ASSIGNMENTS

CROSS REFERENCE TO RELATED APPLICATIONS

This application claims the benefit of U.S. Provisional Patent Application No. 60/800,295, filed May 15, 2006, titled "System and Method for Managing Point of Care Assignments," the contents of which are hereby incorporated by reference herein.

TECHNICAL FIELD

The present invention relates to patient care logging devices and systems and, more particularly, to such devices and systems that automatically detect and log patient encounters with items in a healthcare setting.

BACKGROUND ART

Some existing point-of-care computer systems include interfaces to patient monitors and treatment devices. Some such systems include display screens for rendering information about patients' symptoms, as well as information received from the patient monitors or information related to operation of the treatment devices. In some cases, the computer systems provide instructions to the treatment devices.

Some systems store patient care information, such as information from laboratories, pharmacies and radiology departments. In some instances, this information is stored within a computer that is designed to stay with a patient during the patient's entire stay in a hospital or other medical facility. In other instances, the information is stored in a central server, and the patient computer accesses the server via a wireless computer network.

Some point-of-care systems include keyboards, so caregivers can manually enter information about drugs that are to be administered to patients and information about equipment that is located in the patients' rooms. Some such systems include interfaces to bar code readers and/or radio frequency identification (RF-ID) readers. In these cases, caregivers may use the readers to manually scan barcodes or RF-ID tags on the drug containers or the equipment. One system includes wireless data receivers and means for detecting when a caregiver enters a room.

Existing patient identification systems relate items, such as patient monitors, with patients and ensure that identified items correspond to identified patients. In one such system, a caregiver manually uses a barcodes scanner that is attached to the system to scan barcodes on a patient's wristband, on the caregiver's identification badge and on an item that is to be administered to the patients. The system indicates whether the item matches the patient or there is a discrepancy between the item and the patient. The system also stores information about administered items for billing purposes.

SUMMARY OF THE INVENTION

An embodiment of the present invention provides a per-patient device for automatically logging items that a patient encounters, such as in a medical facility. The per-patient device includes a reader and a portable housing. The portable housing contains a memory and a processor. The processor is coupled to the memory and to the reader. The processor is programmed to automatically determine when an identification transmitter is within a range of the reader and to automatically receive an identification signal transmitted by the identification transmitter. The processor stores information about an item that corresponds to the identification transmitter. This information is stored in the memory. The processor is also programmed to automatically determine when an identification transmitter that corresponds to the patient ceases to be within the range and to automatically determine when the identification transmitter that corresponds to the patient is again within the range.

Optionally, the processor automatically associates the per-patient device with the patient by storing data, indicative of a received identification signal, in the memory.

The identification transmitter may include an identification tag, an active radio frequency identification (RF-ID) tag, a Bluetooth transmitter or another appropriate transmitter. The identification transmitter may include a transponder in an identification tag. In this case, the per-patient device may also include a transmitter that is operative to trigger the transponder. The identification transmitter may include a passive radio frequency identification (RF-ID) tag. In this case, the per-patient device may also include a transmitter that is operative to interrogate the passive RF-ID tag.

As noted, the processor stores information about an item that corresponds to the identification transmitter. This information may include data received from the identification transmitter that corresponds to the item or data obtained as a result of a query that involves data received from the identification transmitter. For example, some or all of the data received from the identification transmitter may be used as an index into a table or a database, and a table or the database may provide some or all of the information that is to be stored.

The item that corresponds to the identification transmitter may be a medical device, an infusion pump, a ventilator, a patient monitor, a pulse oximeter, a surgical device, a surgical instrument, a drug container, a dialysis machine, another patient, caregiver, a person other than the patient, a caregiver and another patient, a radio-frequency identification (RF-ID) smartcard or a fixed structure within a healthcare facility.

The processor may be programmed to ascertain a location of the per-patient device, based on information about the identification transmitter. The processor may be programmed to provide, based on information about the identification transmitter, information about a location of a second item that corresponds to a previously detected identification transmitter. In either case, the item may include a fixed structure within a healthcare facility.

The processor may be programmed to store the information about the item in the memory if the identification transmitter is within a predetermined distance of the reader.

A processor may be programmed to automatically determine when an identification transmitter ceases to be within the range and to modify the information about the item that corresponds to the identification transmitter. In this case, the housing may also contain a wireless network link for coupling the processor to a server, and the processor may also be programmed to send information to the server when an identification transmitter ceases to be within the range. The information sent to the server may include a location of the identification transmitter.

The information about the item may include data indicative of a time at which the identification transmitter was detected. In this case, the processor may automatically determine when an identification transmitter ceases to be within the range. In addition, the processor may store, in the memory, data indicative of a time at which the identification transmitter ceased to be within the range.

The information about the item may include data indicative of a location of the identification transmitter. In this case, the processor may automatically determine when an identification transmitter ceases to be within the range. In addition, the processor may store, in the memory, data indicative of a location at which the previously detected identification transmitter ceased to be within the range.

Optionally, the per-patient device may include a user interface. In this case, when the processor determines the identification transmitter is within the range, the processor may display, on the user interface, information about the item that corresponds to the identification transmitter. The processor may also display, on the user interface, a prompt asking if the item is to be associated with the patient. If an affirmative response to the prompt is received, the processor may store data in the memory to associate the item with the patient according to a first association type. For example, the association type may be "confirmed as an intentional association." If a negative response to the prompt is received, the processor may store data in the memory to associate the item with the patient according to a second association type. For example, the association type may be "confirmed as coincidental." For example, the item may be a medical device intended for another patient in the same room or otherwise within range of the reader. If no response to the prompt is received within a predetermined amount of time, the processor may store data in the memory to associate the item with the patient according to a third association type. For example, the association type may be "automatically associated as coincidental."

The reader may be operative to scan for identification transmitters in any of several modes. The reader may be operative to continuously scan for identification transmitters. Alternatively or optionally, the reader may be operative to intermittently scan for identification transmitters, or to repetitively scan for identification transmitters, or to periodically scan for identification transmitters, or to scan for identification transmitters according to a duty cycle.

The housing may also contain a wireless network link for coupling the processor to a network. In this case, the processor may be programmed to send information, via the network, when the processor determines an identification transmitter is within the range and to send information, via the network, when an identification transmitter ceases to be within the range.

The housing may also contain a wireless link for coupling the processor to a server. In this case, the processor may be programmed to send information to the server when the processor determines an identification transmitter is within the range and to send information to the server when an identification transmitter ceases to be within the range. Optionally, the wireless link may be operative to forward communications from another per-patient device.

Another embodiment of the present invention provides a system for automatically logging items that a patient encounters, such as in a medical facility. The system may include a server and a plurality of portable per-patient devices. Each per-patient device may be communicably linked to the server over an at least partially wireless link. Each per-patient device may include a wireless port for communicating with the server via the at least partially wireless link, a reader and a processor coupled to the wireless port and to the reader. The processor may be programmed to automatically determine when an identification transmitter is within a range of the reader and to automatically receive an identification signal transmitted by the identification transmitter. The processor sends data related to the identification transmitter, via the wireless port, to the server. The processor also automatically determines when an identification transmitter that corresponds to the patient ceases to be within the range and automatically determines when the identification transmitter that corresponds to the patient is again within the range. The server is programmed to store information about items that correspond to identification transmitters that are determined to be within the range.

The server may be programmed to correlate the information about each item with a patient. In this case, the processor in each per-patient device may be programmed to send data that associates the per-patient device with a particular patient to the server.

The information about each item may include data indicative of a time at which the corresponding identification transmitter was detected. In this case, the processor in each per-patient device may be programmed to send information to the server when a previously detected identification transmitter ceases to be detected within the range, and the server may be programmed to store data indicative of a time at which the previously detected identification transmitter ceased to be detected.

A server may be programmed to produce a list of items that correspond to identification transmitters that were detected by a selected per-patient device. The server may be programmed to produce a list of items that correspond to identification transmitters that were detected by a per-patient device associated with a selected patient. Thus server may be programmed to produce a list of per-patient devices that detected a selected identification transmitter. The server may be programmed to produce a list of per-patient devices that detected an identification transmitter that corresponds to a selected item. The server may be programmed to produce a list of patients associated with per-patient devices that detected a selected identification transmitter. The server may be programmed to produce a list of patients associated with per-patient devices that detected a selected item. The server may be programmed to send a message when a previously detected identification transmitter ceases to be detected.

Yet another embodiment of the present invention provides a method for automatically logging items that a patient encounters, such as in a medical facility. The method includes associating a reader with the patient and listening, with the associated reader, for a signal from an information transmitter. The method also includes automatically detecting an information transmitter when the information transmitter is within a range of the reader. Information about an item that corresponds to the detected information transmitter is stored. The method also includes automatically determining when an identification transmitter that corresponds to the patient ceases to be within the range and then automatically determining when the identification transmitter that corresponds to the patient is again within the range.

The transmitter may include a transponder.

Associating the reader with the patient may include detecting a transmitter that corresponds to the patient.

Automatically detecting the information transmitter may include automatically detecting an information transmitter that corresponds to a medical device, an infusion pump, a ventilator, a patient monitor, a drug container, another patient, a caregiver, or a fixed structure within a healthcare facility.

Storing the information about the item may include storing the information if the detected information transmitter is within a predetermined distance.

The method may also include sending information to a server when the information transmitter is detected or when a previously detected information transmitter ceases to be detected within the range.

Listening for the signal from the information transmitter may include continuously transmitting a trigger signal, intermittently transmitting a trigger signal, repetitively transmitting a trigger signal, periodically transmitting a trigger signal, or transmitting a trigger signal according to a duty cycle.

The method may also include producing a list of items that correspond to information transmitters that were detected by a selected reader, producing a list of items that correspond to information transmitters that were detected by a reader associated with a selected patient, producing a list of readers that detected a selected information transmitter, producing a list of readers that detected an information transmitter that corresponds to a selected item, producing a list of patients associated with readers that detected a selected information transmitter, or producing a list of patients associated with readers that detected an information transmitter that corresponds to a selected item.

An embodiment of the present invention provides a computer program product. The computer program product includes a computer-readable medium. Computer instructions are stored on the computer-readable medium. When the instructions are executed by a processor, the processor automatically determines when an identification transmitter is within a range of a reader and automatically receives an identification signal transmitted by the identification transmitter. The processor stores, in a memory, information about an item that corresponds to the identification transmitter. The processor also automatically determines when an identification transmitter that corresponds to a patient ceases to be within the range and automatically determines when the identification transmitter that corresponds to the patient is again within the range.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Figure 1:
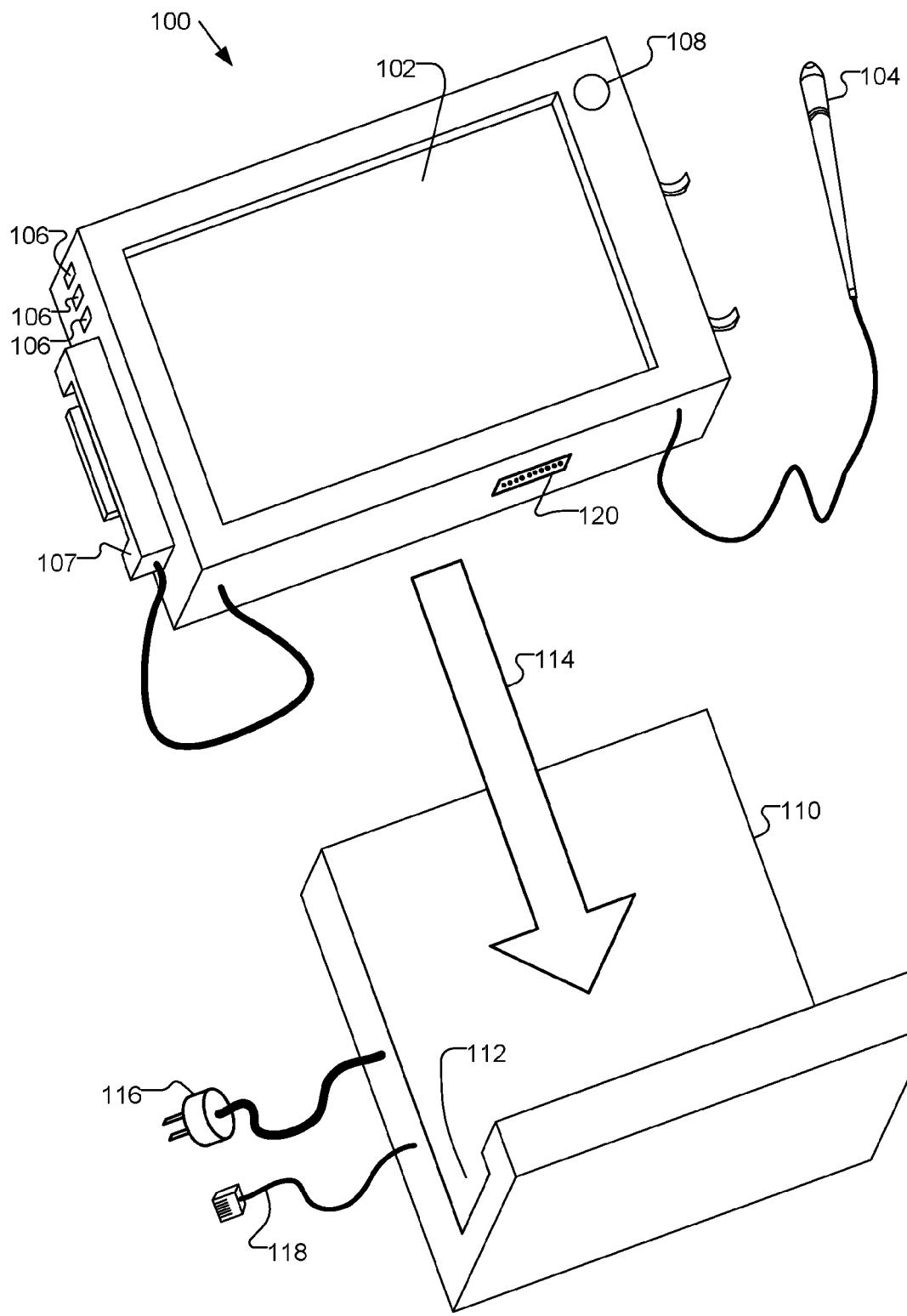
FIG. 1 is a perspective view of a per-patient device, according to one embodiment of the present invention.

In accordance with embodiments of the present invention, methods and apparatus are disclosed for automatically detecting and logging patient encounters with items, such as in a healthcare setting.

The contents of U.S. Provisional Patent Application No. 60/800,295, filed May 15, 2006, titled "System and Method for Managing Point of Care Assignments," are hereby incorporated by reference herein.

DEFINITIONS

As used in this description and accompanying claims, the following terms shall have the meanings indicated below, unless context requires otherwise:

Transmitter—a device that is capable of sending a signal through space. The signal may be a radio frequency (RF) signal, an optical signal or another type of signal.

Receiver—a device that is capable of receiving a signal, through space, from a transmitter.

Transponder—a device that includes a transmitter capable of sending a signal in response to receiving a signal, through space, from another transmitter.

Identification signal—a signal sent by a transmitter, wherein the signal conveys identification information that identifies the transmitter within a universe of transmitter identifications. That is, each transmitter sends identification information that is unique within its universe.

Identification transmitter—a transmitter that sends an identification signal.

Radiofrequency identification (RF-ID) tag—a device that is capable of automatically sending, through space, an identification signal. The identification information identifies the RF-ID tag within a universe of RF-ID tags. That is, each RF-ID tag sends identification information that is unique within its universe. The RF-ID tag may store this identification information and, optionally, other information in a memory, such as in a non-volatile EE-PROM. None, some or all of the other information may be included in the identification signal. An RF-ID tag may be attached to, or included or enclosed in, an item, including a product, an animal or a person, to facilitate automatic identification of the item.

Passive RF-ID tag—an RF-ID tag that does not require an internal power source. A passive RF-ID tag includes a transponder. A passive RF-ID tag sends an identification signal in response to receiving an "interrogation" signal sent by a transmitter. The interrogation signal may provide power necessary for the passive RF-ID tag to send the identification signal. For example, a passive RF-ID tag may send the identification signal by backscattering the interrogation signal.

Active RF-ID tag—an RF-ID tag that has an associated or internal power source. An active RF-ID tag may be capable of sending an identification signal without being powered by a received interrogation signal. An RF-ID tag may transmit an identification signal continuously or intermittently. An active RF-ID tag may, but need not, transmit an identification signal absent an interrogation signal.

Reader—a device that is capable of receiving an identification signal from an identification transmitter. A reader includes a receiver. A reader may also include a transmitter for sending an interrogation signal. If the reader includes a such a transmitter, the reader may operate the transmitter continuously or intermittently.

Listening—operating a receiver so that, if an identification signal is available to be received, the receiver would receive the identification signal. The identification signal may be sent by an identification transmitter sua sponte or as a result of receiving an interrogation signal. Listening may be continuous or intermittent. Listening is an operation performed by a reader.

Scanning—sending an interrogation signal and listening for a responsive identification signal. The interrogation signal may be sent continuously or intermittently, and the listening may be continuous or intermittent. There may be a delay between the end of the interrogation signal and the beginning of the identification signal, or these two signals may overlap in time. Some readers scan.

Smartcard (also referred to as a "contactless smartcard")—a card, typically approximately the size of a credit card, that includes a transmitter or transponder, typically an RF-ID tag.

Item—a thing to which a transmitter or transponder (such as an RF-ID tag) can be attached (or in which the transmitter or transponder can be included or enclosed), such as a patient or a thing that a patient may contact or come close to. Exemplary items include a medical device, a dialysis machine, an infusion pump, a tube, a ventilator, a patient monitor, a pulse oximeter, a surgical instrument, a drug container (such as a bottle, jar, bag or syringe), a bed, a wall, door or ceiling panel within a medical facility, a smartcard, a caregiver, another patient, a visitor and another person.

Encounter—an event during which a patient contacts or comes close to an item. The patient need not be aware of the encounter. For example, the patient may be unconscious, or the patient may simply not notice the encounter. Exemplary encounters include a medical device being brought to a bed in which a patient lies, a caregiver approaching a patient and a patient being brought into an operating room. Contrary to an ordinary dictionary definition, as used herein "encounter" does not imply a conflict.

Automatically Detecting and Logging Patient Encounters with Items

We recognized that automatically detecting and logging patient encounters with items, such as medical devices, drugs or people, would provide data that is valuable for many purposes. For example, such data may be used to identify patients who may have been affected by a contaminated or defective medical device or drug or by a caregiver, visitor or another patient who is infected with a communicable disease. Thus, if an item is later found to be contaminated, defective or infected, all the patients who encountered the item may be identified and treated appropriately. Similarly, data on patient encounters may be used to identify medical devices, caregivers, visitors or other patients who may have been infected by a given patient. Thus, if a patient is found to be infected, all the items that or who encountered the patient may be identified and treated appropriately.

Automatically detecting patient encounters with items requires a device that operates without attention or input from an attendant. The device should automatically associate itself with a patient. In addition, the device should automatically detect when the device becomes separated from the patient and then returned to the patient (or the patient returns to the device), so data provided by the device reflects encounters with the device that occur only while the device is in the presence of the patient. Furthermore, the device can send an alarm signal when the device becomes separated from the patient.

Prior art point-of-care systems and patient identification systems do not automatically associate themselves with patients, nor do such systems automatically detect when they becomes separated from the patients. Some such prior art systems require a caregiver to manually enter data via a keyboard or to initiate a scan of a patient's wrist identification bracelet and the caregiver's own identification badge before the system associates itself with the patient or can associate a tagged item with the patient. Furthermore, prior art devices do not capture information about items that are not used for treating a patient, such as visitors or other patients housed in the same room as the patient.

Automatic detection and logging of patient encounters involves automatically detecting an encounter with an item, without requiring a caregiver to manually trigger a system to scan for or detect the item. A caregiver need not even be present for automatic detection to occur. Embodiments of the present invention provide methods and apparatus for automatically detecting and logging patient encounters with items.

We also recognized that automatically detecting and logging when a patient encounter ends, i.e., when a patient ceases to be close to an item, would provide valuable data. For example, when an infusion pump or another medical device is removed from a patient's room, automatically sending a message to a medical equipment inventory and maintenance department enables the department to expeditiously retrieve the medical device and prepare it for a subsequent patient. In addition, as noted, detecting when a patient becomes separated from a device enables the device to raise an alarm.

FIG. 1 is a perspective view of one embodiment of the present invention. A portable, battery-powered per-patient device 100 includes a touch-sensitive screen 102, a processor and memory (not visible). The touch-sensitive screen 102 provides all or part of a user interface. The touch-sensitive screen 102 may display a virtual keyboard, menu options, virtual buttons or other controls, such as pull-down lists, check boxes and text boxes. Optionally or alternatively, the per-patient device 100 may include a separate keyboard or buttons (not shown). A user, such as a caregiver, may interact with the processor via the touch-sensitive screen 102, the keyboard or the buttons.

The per-patient device 100 also includes a radio frequency identification (RF-ID) reader (not visible). The RF-ID reader may be external to a housing of the per-patient device 100, or the RF-ID reader may be external to the housing and coupled to the processor, such as via a suitable electrical connector.

In use, such as in a hospital or other healthcare facility, a separate per-patient device 100 is assigned to each patient. The per-patient device 100 may be attached to the patient's bed, wheelchair, walker or the like. If the patient is ambulatory, the patient may carry the per-patient device 100. The per-patient device 100 is intended to remain with the patient during the patient's stay in the healthcare facility.

The per-patient device 100 can automatically detect an RF-ID-tagged item, such as a medical device, a drug or a person, that comes within a range of the device 100. In actuality, the per-patient device 100 automatically detects an RF-ID tag that comes within range of the reader. However, for simplicity of explanation, we will refer to detecting an RF-ID tag or an item coming within range of the per-patient device 100.

In a typical context in which the per-patient device 100 is used, each patient wears a wrist bracelet, identification badge or the like, with an RF-ID tag. If passive RF-ID tags are used, the RF-ID reader scans for the RF-ID tags. If active RF-ID tags are used, the RF-ID reader listens for identification signals from the RF-ID tags. If active RF-ID tags are used, the RF-ID reader may, but need not, scan for RF-ID tags. A mixture of passive and active RF-ID tags may be used. Optionally or alternatively, other types of transmitters or transponders may be used instead of RF-ID tags. In one embodiment, a Bluetooth transmitter is used, however any suitable transmitter may be used. For simplicity of explanation, the description of this and other embodiments assumes RF-ID tags are used; however, these descriptions also apply to embodiments in which other types of transmitters or transponders are used.

The per-patient device 100 may detect when the device 100 is brought close to a patient, and the per-patient device 100 may, as a result, automatically associate itself with the patient. The per-patient device 100 may be inhibited from associating itself with a patient until the device 100 is enabled. For example, while one or more per-patient devices 100 are stored, before being distributed to patients, the devices 100 may be inhibited from associating themselves with patients. When a per-patient device is distributed to a patient, the device 100 may be activated, such as by pressing a button (not shown) on the device 100 or by activating a control displayed on the touch-sensitive screen 102. Activating the per-patient device 100 enables the device 100 to associate itself with the next patient RF-ID tag that the device 100 detects.

The per-patient device 100 may use the screen 102 to display information about the detected patient or the detected RF-ID tag. Optionally, the per-patient device 100 prompts a caregiver to enter information about the detected patient, such as patient name, and/or to verify that the detected patient should be associated with the per-patient device 100. The per-patient device 100 may automatically detect and log other patients that come within the range of the per-patient device 100.

Other items that come close to, or come into contact with, a patient also may have RF-ID tags. For example, caregivers and visitors may wear identification badges having RF-ID tags, and RF-ID tags may be attached to medical equipment, drug containers and the like. These items may, of course, include items that the patient may approach, in addition to items that may approach or be brought close to the patient. Thus, when an item comes within range of the per-patient device 100, the device may detect and log the presence of the item.

When a previously detected RF-ID tag is no longer within range of the per-patient device 100, such as because a caregiver leaves the patient's room or a medical device is removed from the patient's room, the per-patient device 100 ceases to detect the previously detected RF-ID tag and logs this fact. Information, such as a time and date on which an RF-ID tag is detected or ceases to be detected, may be included in the log maintained by the per patient device 100.

RF-ID tags may be attached to, or embedded in, fixed structures within a healthcare facility to facilitate detecting movement of the patient within the facility. These fixed structures may include walls, ceilings, doors, floors, windows, pipes, lamp posts and the like. The fixed structures may be located inside or outside buildings. "Fixed" means the structures may not be easily moved from place to place, although the structures may move, such as in the way a door pivots to open or close. These RF-ID tags are referred to as "location-specific" RF-ID tags, and their locations are noted. As the patient moves about with the per-patient device 100, the device 100 detects and ceases to detect these location-specific RF-ID tags. Based on the currently detected location-specific RF-ID tag(s), and optionally a history of location-specific RF-ID tags that have ceased to be detected, the per-patient device 100 may infer a location of the patient within the healthcare facility.

Optionally, the per-patient device 100 may use other techniques or information to infer or refine the location of the patient. These other techniques and information include a received signal strength indication (RSSI) of the signal(s) received from the location-specific RF-ID tag(s), a time between transmission of an interrogation signal and receipt of an identification signal, triangulation and other techniques or information well known in the art. The per-patient device 100 logs a time when, and a location where, the device 100 detects each location-specific RF-ID tag. Similarly, the per-patient device 100 logs when and where the device 100 ceases to detect each location-specific RF-ID tag. Optionally or alternatively, the per-patient device 100 logs a current location and/or a location history of the patient.

Using RSSI or the other techniques referenced above, the per-patient device 100 may ascertain a distance between an RF-ID tag and the device 100.

Optionally, the per-patient device 100 includes a wireless port (not shown) for connection to a wireless computer network. A server (not shown) may be connected to the wireless network, either directly or via a wired link. The per-patient device 100 may communicate, via the wireless computer network, with other per-patient devices and/or with the server, as discussed in more detail below. The logs may be maintained on the per-patient device 100, on the server or on both.

Optionally, the per-patient device 100 includes a barcode scanner 104, with which a caregiver may scan a barcode on an item, such as if the item does not have an RF-ID tag.

Optionally, the per-patient device 100 includes ports 106, by which medical devices, such as infusion pumps, medical monitors, such as heart monitors, and the like may be connected to the device 100. Via these ports 106, the per-patient device 100 may receive information from the medical devices, monitors, etc. For example, the medical monitors may send physiological data, such as heart rate, blood pressure and respiration rate, to the per-patient device 100 for logging or alarm generation. In addition, the per-patient device 100 may send instructions, via the ports 106, to the medical devices, monitors, etc. For example, the per-patient device 100 may send instructions, such as an infusion rate, to an infusion pump.

The per-patient device 100 may include other peripheral devices, such as a telephone handset 107 for use by a patient and/or a caregiver. The per-patient device 100 uses a packet-based protocol, such as voice over Internet protocol (VoIP) to send and receive voice signals over the wireless computer network to and from other per-patient devices 100 and/or a gateway to a telephone system. Similarly, a camera 108 may be used to send still pictures or motion video to another per-patient device 100, a computer coupled to the wireless network or another computer or gateway.

Optionally, the per-patient device 100 may be coupled to a docking station 110, by inserting the device 100 into a receiving portion 112 of the docking station 110, as indicated by an arrow 114. The docking station 110 may be attached to a bed, wall mount or other structure. The docking station 110 may be connected to a power source, such as a wall outlet or a socket on a patient bed, via a power connector 116. The docking station may be connected to a computer network via a network cable 118.

When docked, the per-patient device 100 is electrically coupled to the docking station 110 via a connector 120 on the device 110 and another connector (not visible) on the docking station 110. Batteries (not visible) in the per-patient device 100 may be charged while the device 100 is so docked. In addition, the per-patient device 100 may establish a network connection, via the docking station 110 and the network cable 118, to a computer network.

Figure 2:
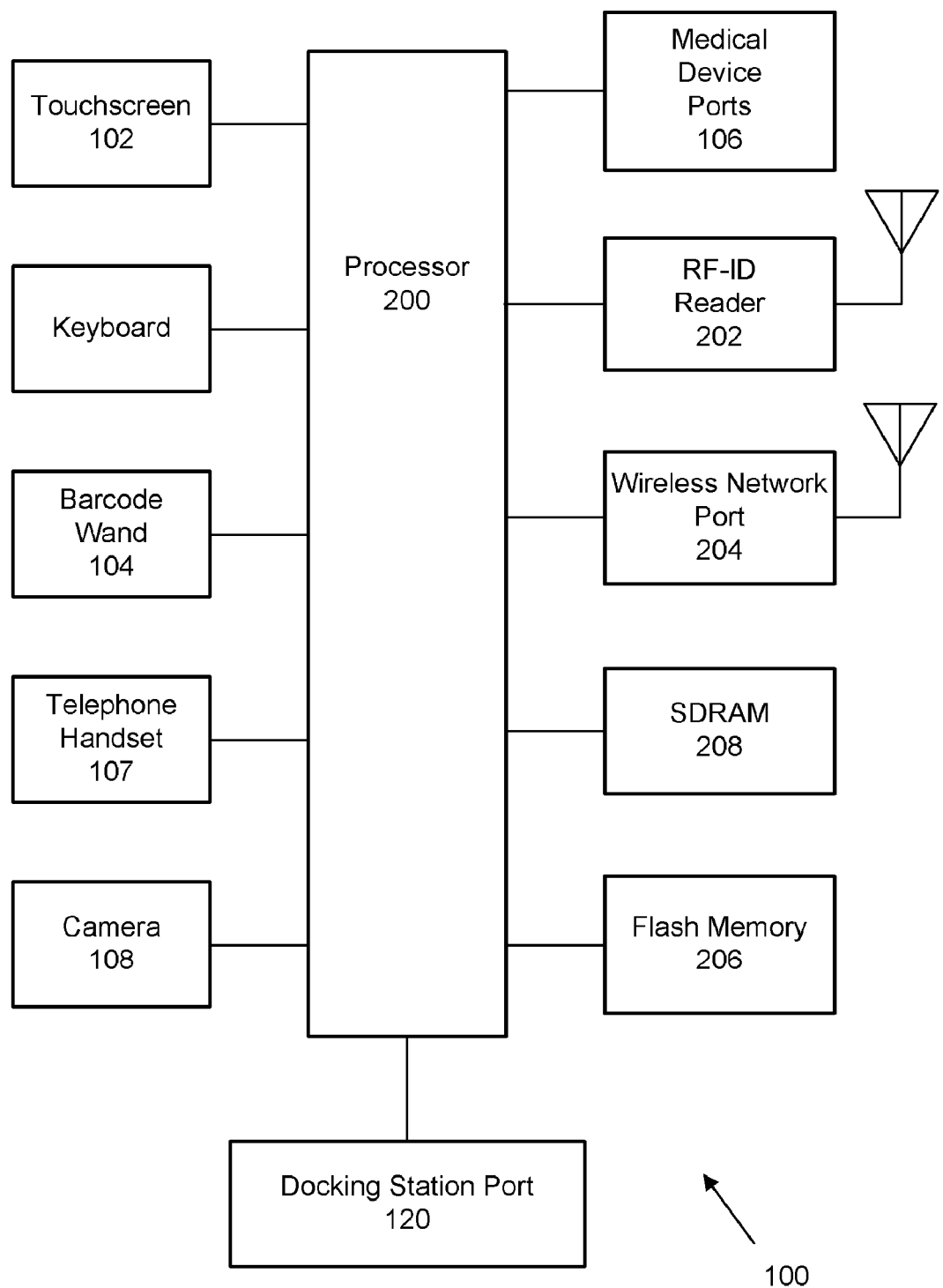
FIG. 2 is a block diagram of the per-patient device of FIG. 1, according to one embodiment of the present invention.

FIG. 2 is a block diagram of the per-patient device 100 of FIG. 1. The block diagram shows the peripheral devices discussed above, including devices not visible in FIG. 1, such as the processor 200, RF-ID reader 202 and wireless network port 204. Although not shown in FIG. 2, the per-patient device 100 may include a bus to interconnect the processor 200 and the peripheral devices. The per-patient device 100 may also include other circuits (not shown) to automatically connect the battery, processor 200 and/or peripherals to components in the docking station 110, as discussed above.

The per-patient device 100 may include one or more types of memory. For example, a non-volatile memory 206, such as a flash memory, may be used to store instructions for the processor while the per-patient device 100 is powered down. When the per-patient device 100 is turned on, these instructions may be copied to a faster memory, such as a synchronous dynamic random access memory (SDRAM) 208, by a basic input/output system (BIOS) or the like. Once the SDRAM 208 is loaded with instructions, the processor executes the instructions stored in the SDRAM 208. These instructions control the operation of the processor; that is, the processor is programmed by these instructions to perform the operations described herein.

The non-volatile memory 206 may also store data while the per-patient device 100 is powered down. For example, patient medical data, such as data that corresponds to an electronic patient chart, and information about items that the patient has encountered may be stored in the non-volatile memory 206 by the processor, so if the battery becomes exhausted, this data will be available after the battery is recharged or replaced.

Figure 3:
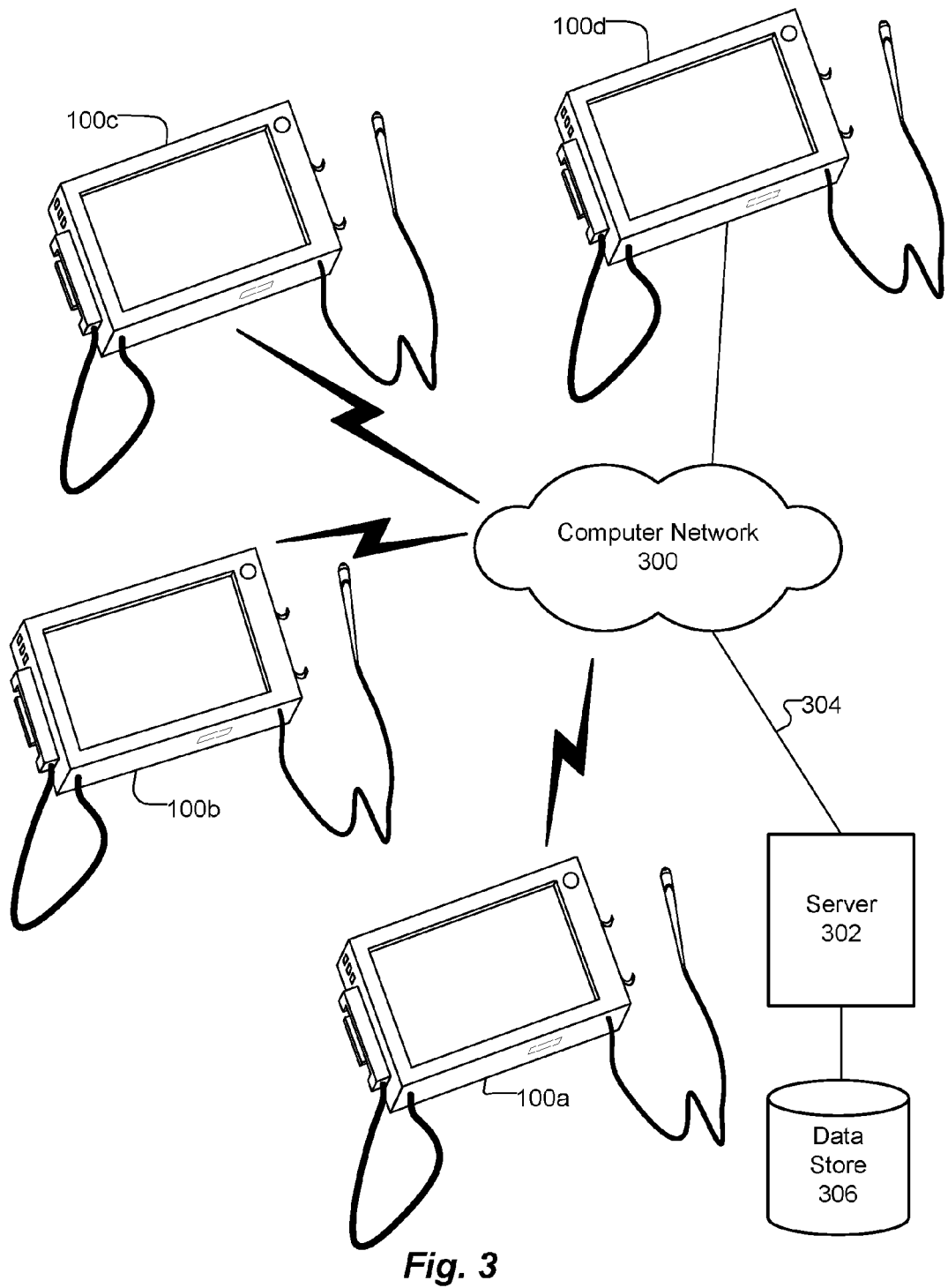
FIG. 3 is a block diagram of an exemplary context, in which embodiments of the present invention may be used.

FIG. 3 is a block diagram of an exemplary context, in which embodiments of the present invention may be used. As noted, one or more per-peripheral devices 100a-d may communicate, via a wireless computer network 300, with a server 302. The server 302 may be connected to the wireless network 300 via a wireless connection or, as shown in FIG. 3, via a wired connection 304. The server 302 maintains a data store 306, in which the server 302 may log information about encounters the per-patient devices 100a-d have with items. Because the per-patient devices 100a-d are coupled via wireless connections, the devices 100a-d may continue to communicate with the server 302 while a patient moves or is moved, such as between the patent's room and an operating room. As noted, the location-specific RF-ID tags enable the per-patient devices 100a-d to detect their respective locations within a medical facility and report those locations to the server 302, as the devices 100a-d are moved. The server 302 stores this information in the data store 306; thus, the location of a patient may be ascertained by querying the server 302.

Figure 4:
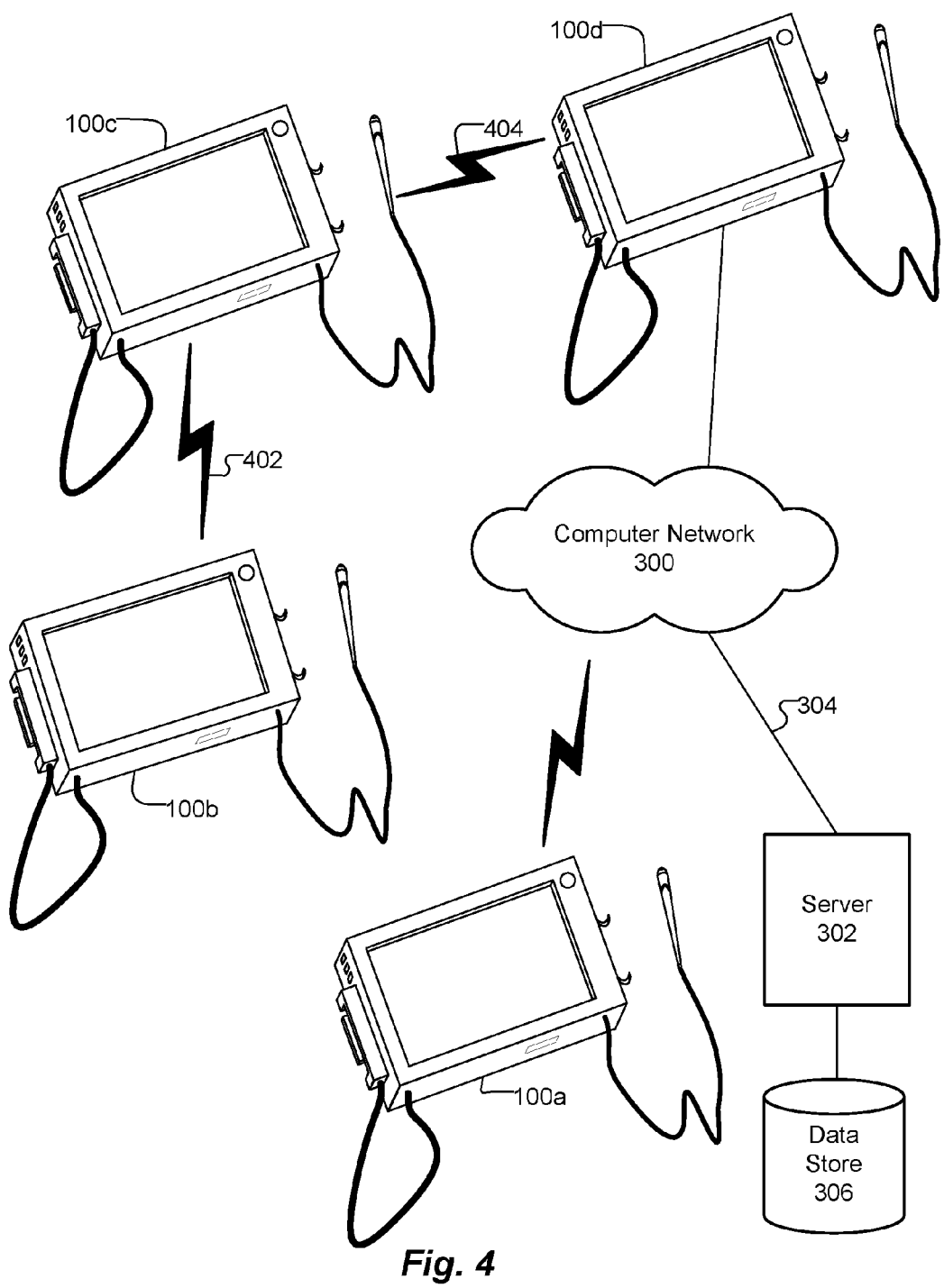
FIG. 4 is a block diagram of another exemplary context in which embodiments of the present invention may be used.

As noted, when a per-patient device 100 is docked, the device 100 may establish a wired network connection through the docking station 110. FIG. 4 shows another exemplary context in which embodiments of the present invention may be used. The context shown in FIG. 4 is similar to the context shown in FIG. 3, except one of the per-patient devices 100d is docked and has established a wired connection 400 to the computer network 300. In addition, two of the per-patient devices 100b and 100c do not have wireless links to the computer network 300. This may be because the per-patient devices 100b-c are out of range of the wireless computer network 300, radio frequency interference (RFI) in the vicinity of the devices 100b-c or of an access point (not shown) of the wireless network 300 prevents establishing a wireless link between the devices 100b-c and the network 300, all or part of the wireless network 300 has failed or for some other reason.

The per-patient devices 100a-d may include a capability to form a mesh network (sometimes referred to as a peer-to-peer network) to overcome the inability to establish wireless links directly with the computer network 300. Momentarily referring back to FIG. 2, it can be seen that each per-patient device 100a-d includes a wireless network port 204. The wireless network port 204 may be used to wirelessly communicate with other per-patient devices 100 to form a mesh network, as shown in FIG. 4. For example, as shown in FIG. 4, the per-patient device 100b establishes a wireless link 402 with the other per-patient device 100c, and the other device 100c forwards communications, via a second peer-to-peer link 404, to the third per-patient device 100d. This peer-to-peer linking continues until a per-patient device, such as the device 100d, that has a wired or wireless connection to the computer network 300 is reached. The per-patient device 100d forward communications from the devices 100b-c to the network 300 via the connection 400.

Figure 5:
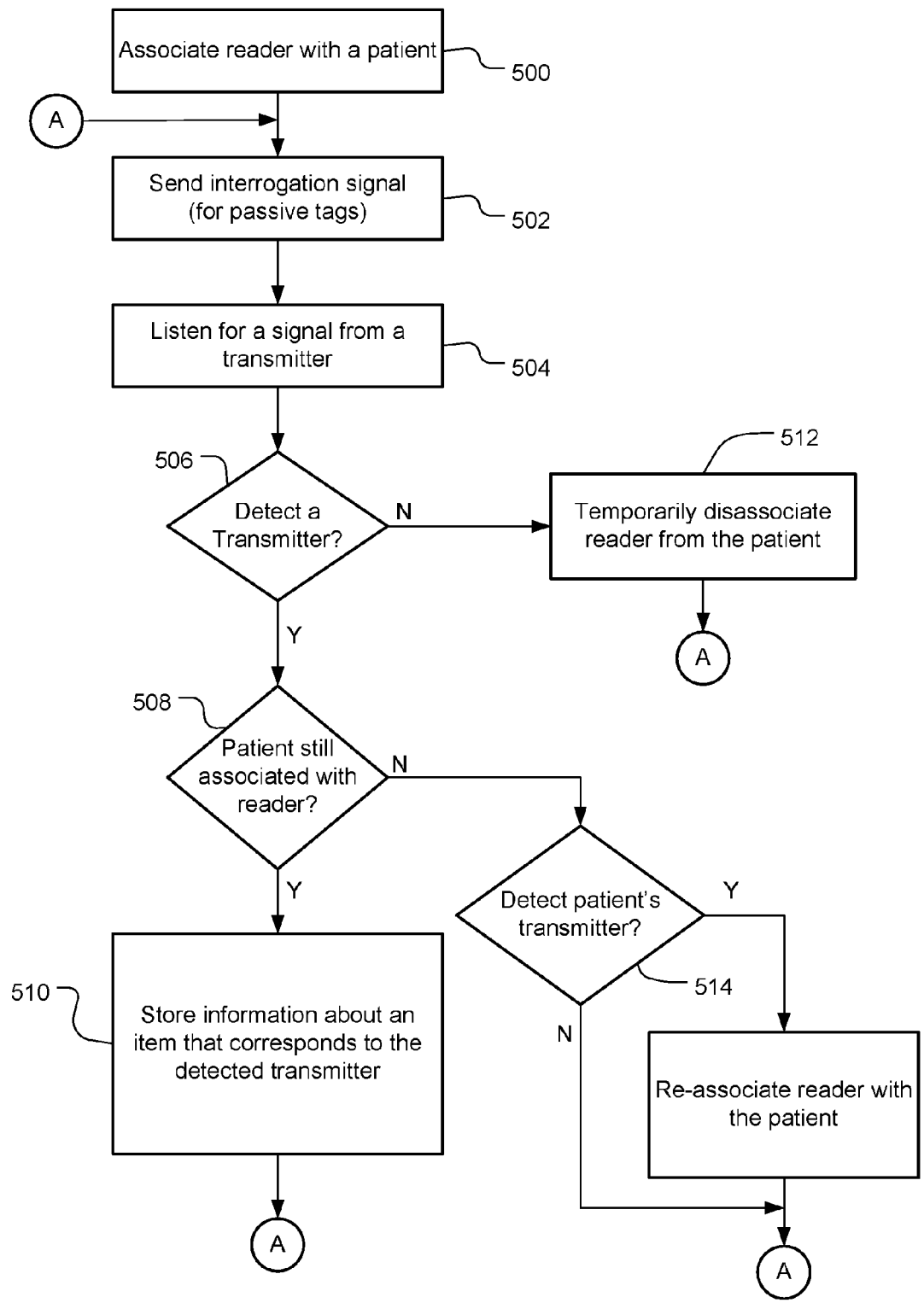
FIG. 5 is a flowchart that illustrates operations performed, according to one embodiment of the present invention.

FIG. 5 is a flowchart that illustrates operation of one embodiment of the present invention. At 500, a reader is associated with a patient. This association may be automatic, such as by the reader detecting an information transmitter in the patient's wristband, badge, etc. (collectively "patient ID"). Optionally or alternatively, this association may be manual or semi-automatic. For example, a caregiver may enter data via a user interface to associate the reader with the patient, or the caregiver may confirm a proposed association with a patient ID that the reader has automatically detected.

At 502, if the patient ID is passive, an interrogation signal is sent.

At 504, the reader listens for a signal from one or more information transmitters. At 506, if an information transmitter is detected, control passes to decision block 508. At 508, if the patient is still associated with the reader, control passes to block 510, where information about an item that corresponds to the detected information transmitter is stored. This information may include information send by the identification transmitter and/or other information, such as a current time and date and a location of the reader (if known). Control then returns to 502, to repeat the process.

If, at 506, no identification transmitter is detected, it may be assumed that the patient and the reader have become separated, inasmuch as the patient's ID should be detected. If the patient's ID is not detected, at 512 the reader is temporarily disassociated from the patient. To accommodate transient errors in transmission or reception of identification signals from the patient's ID, the disassociation may be deferred until the patient's ID is not detected for a predetermined number of consecutive attempts to read the patient's ID. Once the reader is temporarily disassociated from the patient, control returns to 502.

At 506, once a transmitter is detected, control passes to 508. If, at 508, the reader is not associated with the patient, control passes to 514. If, at 514, the patient's ID is once again detected, control passes to 516, where the reader is re-associated with the patient, and then control returns to 502. On the other hand, if at 514 the patient's ID is still not detected, control returns to 502, and the reader remains temporarily disassociated from the patient.

A reader may detect tags quite frequently, because visitors, other patients, medical devices, etc. that have ID tags may come within range of the reader quite often. Some of these items are intended to provide medical care for a patient that is associated with the reader, i.e., the items are part of a diagnostic or therapeutic regimen for the patient. Other of these items are encountered coincidentally, i.e., without an intention of providing medical care to the patient.

The per-patient device 100 may maintain a table in memory to correlate identification information with item types, as well as to store descriptive information about the items in a medical facility. Some of this descriptive information may be static, such as information about infusion pumps and the like. Other of this information may be dynamic, such as information about visitors who are assigned ID badges for the durations of their visits. Optionally or alternatively, the server 302 may maintain this information and provide the information to the per-patient device 100 upon request. Thus, the per-patient device 100 can distinguish identification information that was sent by tags associated with medical devices, caregivers, visitors, etc. The per-patient device 100 may act differently, depending on the type of item the device 100 has detected. In some cases, the per-patient device 100 may prompt for input from a caregiver for additional information about a detected item or for instructions on how the detected item should be treated. In other cases, the per-patient device 100 may process the detected item automatically, i.e., without user interaction.

Figure 6:
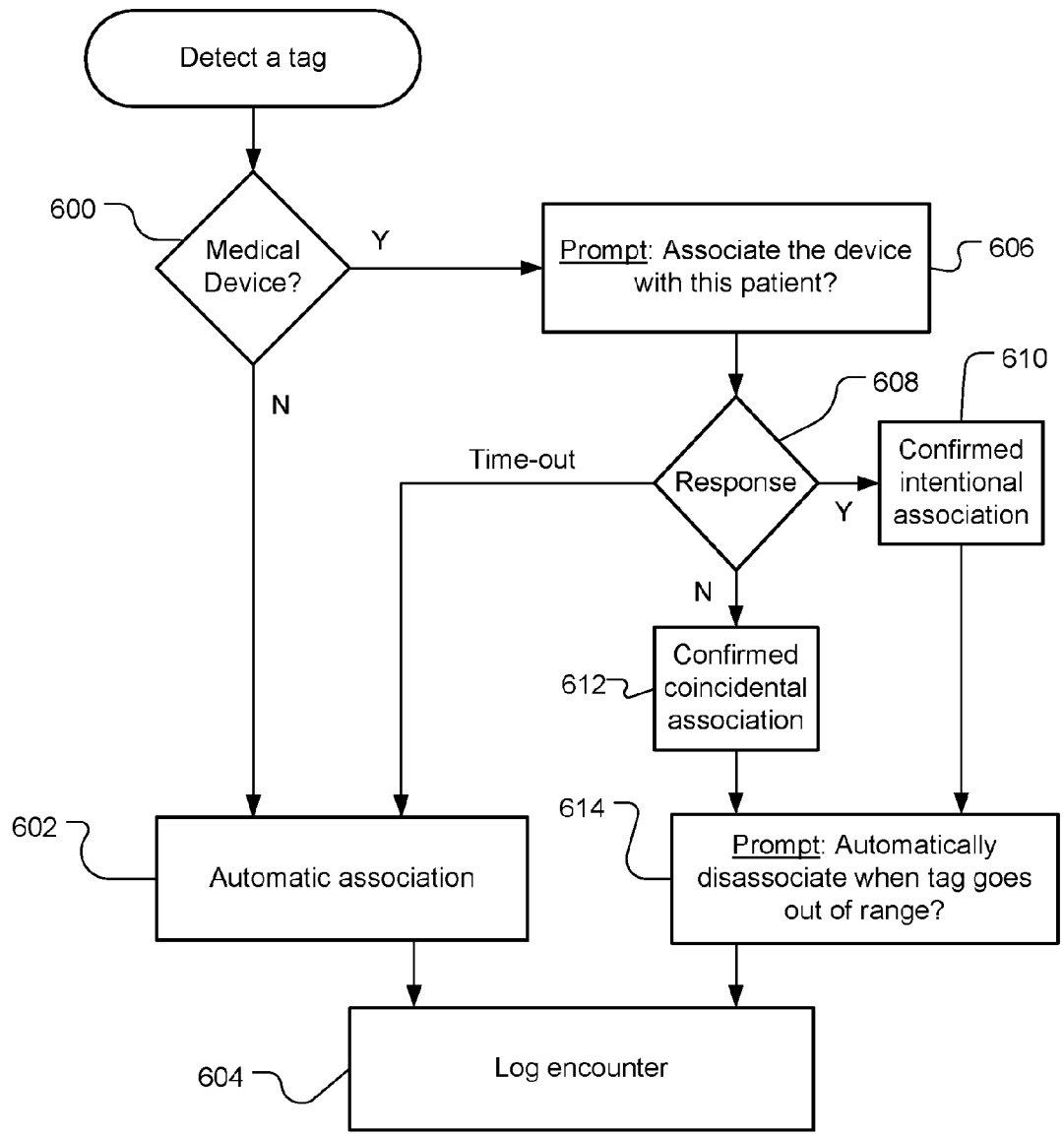
FIG. 6 is a more detailed flowchart that illustrates operations performed when a tag is detected by a reader, according to one embodiment of the present invention.

FIG. 6 is a more detailed flowchart that illustrates operations performed when a tag is detected by a reader, according to one embodiment of the present invention. At 600, if an item other than a medical device is detected, control passes to 602, where the item is automatically associated with the patient, i.e., the item is associated without prompting for input. The encounter is logged at 604. The log entry includes the type of association, i.e., "automatic and coincidental." The log entry also includes the type of the item. Types include caregiver, another patient, visitor, landmark (i.e., a location-specific tag) and other or unknown. Unknown types may be tags that are not associated with items that can be predicted to be in the medical facility. For example, many retail goods, such as tags attached to articles of clothing, include RF-ID tags to facilitate inventorying and checkout. Such articles of clothing may be worn by visitors to the medical facility. Unknown tags may be ignored or logged. The bulk of encounters may be with items other than medical devices; thus, most encounters will not produce a prompt for caregiver input.

On the other hand, at 600, if a medical device is detected, control passes to 606, where a prompt asks if the detected device should be associated with the patient. The prompt may include information about the detected item, such as a tag ID, manufacturer, type, model, etc. This information may be sent by the information transmitter and/or retrieved from the above-described table or the server 302. At 608, the flowchart branches, depending on a response to the prompt. If a user indicates the detected device should be associated with the patient, control passes to 610, where the association is deemed to be "confirmed as an intentional association." On the other hand, if the user indication is negative, control passes to 612, where the association is deemed to be "confirmed as coincidental." That is, the user indicated the item that corresponds to the detected tag is not part of the patient's diagnostic or therapeutic regimen. The item may be a medical device intended for another patient in the same room or otherwise within range of the reader.

In either case, at 614, the per-patient device 100 prompts the user to ask if the item should be automatically disassociated, i.e., without prompting or user input, when the item's tag goes out of range of the reader. An item may temporarily become separated from the patient. For example, a therapy device may remain in the patient's room while the patient is temporarily taken to a radiology department. In such a case, the user may respond to the prompt at 614 in the negative. If the patient and the per-patient device 100 are taken from the room, and the item remains in the room, the device 100 does not prompt when the item's tag goes out of range of the reader. Instead, the per-patient device 100 logs a temporary disassociation and continues listening for the item's tag. When the patient (and the per-patient device 100) are returned to the room, the device 100 detects the item's tag again and automatically re-associates the item with the patient, i.e., without prompting. The user may also be prompted (not shown) to ask if an alarm should be raised if the item's tag goes out of range of the reader. The responses to the prompts 606 and 614, as well as information about the item, the time and (optionally) the location of the reader, are logged at 604.

If no response to the first prompt 606 is received within a predetermined timeout period, control passes from 608 to 602, where the item is automatically associated with the patient, as discussed above. The encounter is logged at 604.

If plural tags are detected, the prompts 606 and 614 may include pull-down lists or other controls by which the user may indicate for which item he/she is providing a response.

Although not shown in the flowcharts of FIGS. 5 and 6, optionally, the per-patient device 100 or the server 302 may ascertain whether a detected medical device, drug or the like has been approved or ordered for the patient that is associated with the per-patient device 100. Approved and ordered items may be listed and correlated with patients in the data store 306 connected to the server 302 and/or in the memory 206 and/or 208 of the per-patient device 100. When the per-patient device 100 detects an item, the device 100 may query the list of approved and ordered items to ascertain if the detected item should or should not be administered to the patient. The list may include "wildcard" entries of items that may be administered to any patient and/or items that must not be administered to any patient, absent an explicit list entry for a given patient. If the detected item must not be administered to the patient, of the list contains no information about whether the item may be administered to the patient, the per-patient device 100 may display an appropriate indication on the touch-sensitive screen 102 and, optionally, send an alarm message.

As a result of the logging of association types and (optionally) locations, the per-patient device 100 or the server 302 (FIGS. 4 and 5) may be queried to ascertain a status of a specified item. For example, a user may query to ascertain whether a specified therapeutic device is currently associated with a patient, not associated with any patient or temporarily disassociated with a patient, pending return of the patient. Because the patient's per-patient device 100 may report the current location of the patient, the response to the query may include the patient's current location, such as "radiology," from which the user may be able to infer an amount of time in which the patient is likely to be returned to his/her room and reunited with the therapeutic device. Furthermore, a user may query the per-patient device 100 or the server 302 to ascertain the number and last detected locations of all items of a specified type. For example, the user may query for a list of all infusion pumps that are available, i.e., not associated with any patient.

The per-patient device 100 or the server 302 may also be queried for information about other relationships. For example, if a batch of drugs or implants is found to be contaminated or defective, all the patients that received doses of the drugs or the implants may be identified, and remedial action may be taken.

A per-patient device has been described as including a processor controlled by instructions stored in a memory. The memory may be random access memory (RAM), read-only memory (ROM), flash memory or any other memory, or combination thereof, suitable for storing control software or other instructions and data. Some of the functions performed by the per-patient device have been described with reference to flowcharts. Those skilled in the art should readily appreciate that functions, operations, decisions, etc. of all or a portion of each block, or a combination of blocks, of the flowcharts may be implemented as computer program instructions, software, hardware, firmware or combinations thereof Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various illustrative data structures, one skilled in the art will recognize that the system may be embodied using a variety of data structures. Furthermore, disclosed aspects, or portions of these aspects, may be combined in ways not listed above. Accordingly, the invention should not be viewed as limited.

What is claimed is:

1. A per-patient device for association with a patient and for automatically logging items that the patient encounters, each such item having a corresponding respective first identification transmitter, and the patient having a corresponding second identification transmitter, the per-patient device comprising:
    a reader; and
    a portable housing containing:
        a memory; and
        a processor coupled to the memory and to the reader, the processor being programmed to:
            automatically determine when a first identification transmitter is within a range of the reader;
            automatically receive an identification signal transmitted by the first identification transmitter and store, in the memory, information about an item that corresponds to the first identification transmitter, such that the information is stored beyond end of an encounter between the patient and the item;
            automatically determine when the second identification transmitter that corresponds to the patient ceases to be within the range; and
            automatically determine when the second identification transmitter that corresponds to the patient is again within the range.

2. A per-patient device, as defined in claim 1, wherein the processor is programmed to automatically associate the per-patient device with the patient by storing data, indicative of a received identification signal, in the memory.

3. A per-patient device, as defined in claim 1, wherein each of the first and the second identification transmitter comprises a transmitter in an identification tag.

4. A per-patient device, as defined in claim 1, wherein each of the first and the second identification transmitter comprises an active radio frequency identification (RF-ID) tag.

5. A per-patient device, as defined in claim 1, wherein each of the first and the second identification transmitter comprises a Bluetooth transmitter.

6. A per-patient device, as defined in claim 1, wherein:
    each of first and the second identification transmitter comprises a transponder in an identification tag; the per-patient device further comprising:
    a transmitter operative to trigger the transponder.

7. A per-patient device, as defined in claim 1, wherein:
    each of the first and the second identification transmitter comprises a passive radio frequency identification (RF-ID) tag; the per-patient device further comprising:
    a transmitter operative to interrogate the passive RF-ID tag.

8. A per-patient device, as defined in claim 1, wherein the information about the item comprises data received from the first identification transmitter that corresponds to the item.

9. A per-patient device, as defined in claim 1, wherein the information about the item comprises data obtained as a result of a query that involves data received from the first identification transmitter.

10. A per-patient device, as defined in claim 1, wherein the item comprises a medical device.

11. A per-patient device, as defined in claim 10, wherein the item comprises an infusion pump.

12. A per-patient device, as defined in claim 10, wherein the item comprises a ventilator.

13. A per-patient device, as defined in claim 10, wherein the item comprises a patient monitor.

14. A per-patient device, as defined in claim 10, wherein the item comprises a pulse oximeter.

15. A per-patient device, as defined in claim 10, wherein the item comprises a surgical device.

16. A per-patient device, as defined in claim 10, wherein the item comprises a surgical instrument.

17. A per-patient device, as defined in claim 1, wherein the item comprises a drug container.

18. A per-patient device, as defined in claim 10, wherein the item comprises a dialysis machine.

19. A per-patient device, as defined in claim 1, wherein the item comprises another patient.

20. A per-patient device, as defined in claim 1, wherein the item comprises a caregiver.

21. A per-patient device, as defined in claim 1, wherein the item comprises a person, other than the patient, a caregiver and another patient.

22. A per-patient device, as defined in claim 1, wherein the item comprises a radio-frequency identification (RF-ID) smartcard.

23. A per-patient device, as defined in claim 1, wherein the item comprises a fixed structure within a healthcare facility.

24. A per-patient device, as defined in claim 1, wherein the information about the item comprises information about a location of the item.

25. A per-patient device, as defined in claim 24, wherein the item comprises a fixed structure within a healthcare facility.

26. A per-patient device, as defined in claim 1, wherein the processor is programmed to ascertain a location of the per-patient device, based on information about the first identification transmitter.

27. A per-patient device, as defined in claim 26, wherein the item comprises a fixed structure within a healthcare facility.

28. A per-patient device, as defined in claim 1, wherein the processor is programmed to provide, based on information about the first identification transmitter, information about a location of a second item that corresponds to a previously detected first identification transmitter.

29. A per-patient device, as defined in claim 28, wherein the item comprises a fixed structure within a healthcare facility.

30. A per-patient device, as defined in claim 1, wherein the processor is programmed to store the information about the item in the memory if the first identification transmitter is within a predetermined distance of the reader.

31. A per-patient device, as defined in claim 1, wherein the processor is programmed to:
automatically determine when the first identification transmitter ceases to be within the range; and
responsive to determining that the first identification transmitter ceased to be within the range, modify the information about the item that corresponds to the first identification transmitter.

32. A per-patient device, as defined in claim 31, wherein:
the housing further contains a wireless network interface configured to couple the processor to a server; and
the processor is programmed to send information, via the network interface, to the server in response to determining that the first identification transmitter ceased to be within the range.

33. A per-patient device, as defined in claim 32, wherein the processor is programmed to:
ascertain a location of the first identification transmitter; and
send information about the ascertained location of the first identification transmitter to the server.

34. A per-patient device, as defined in claim 1, wherein:
the processor is programmed to:
automatically send information about the item to the server, such that the information about the item comprises data indicative of a time at which the first identification transmitter was detected;
automatically determine when the first identification transmitter ceases to be within the range; and
store, in the memory, data indicative of a time at which the first identification transmitter ceased to be within the range.

35. A per-patient device, as defined in claim 1, wherein the processor is programmed to:
ascertain a location of the first identification transmitter;
store the information about the item, such that the information comprises data indicative of the ascertained location of the first identification transmitter;
automatically determine when the first identification transmitter ceases to be within the range; and
store, in the memory, data indicative of a location at which the previously detected first identification transmitter ceased to be within the range.

36. A per-patient device, as defined in claim 1, further comprising:
a user interface; and
wherein the processor is programmed to:
when the processor determines the first identification transmitter is within the range, display on the user interface:
information about the item that corresponds to the first identification transmitter; and
a prompt asking if the item is to be associated with the patient; and
if an affirmative response to the prompt is received, store data in the memory to associate the item with the patient according to a first association type.

37. A per-patient device, as defined in claim 36, wherein the processor is programmed to, if a negative response to the prompt is received, store data in the memory to associate the item with the patient according to a second association type.

38. A per-patient device, as defined in claim 36, wherein the processor is programmed to, if no response to the prompt is received within a predetermined amount of time, store data in the memory to associate the item with the patient according to a third association type.

39. A per-patient device, as defined in claim 1, wherein the reader is operative to continuously scan for first identification transmitters.

40. A per-patient device, as defined in claim 1, wherein the reader is operative to intermittently scan for first identification transmitters.

41. A per-patient device, as defined in claim 1, wherein the reader is operative to repetitively scan for first identification transmitters.

42. A per-patient device, as defined in claim 1, wherein the reader is operative to periodically scan for first identification transmitters.

43. A per-patient device, as defined in claim 1, wherein the reader is operative to scan for first identification transmitters according to a duty cycle.

44. A per-patient device, as defined in claim 1, wherein:
the housing further contains a wireless network interface configured to couple the processor to a network; and
the processor is programmed to:
send information, via the network, when the processor determines the first identification transmitter is within the range; and
send information, via the network, when the first identification transmitter ceases to be within the range.

45. A per-patient device, as defined in claim 1, wherein:
the housing further contains a wireless network interface configured to couple the processor to a server; and
the processor is programmed to:
send information to the server when the processor determines the first identification transmitter is within the range; and
send information to the server when the first identification transmitter ceases to be within the range.

46. A per-patient device, as defined in claim 45, wherein the wireless network interface is configured to forward communications from another per-patient device.

47. A system for automatically logging items that a patient encounters, each such item having an associated respective first identification transmitter, and the patient having an associated second identification transmitter, the system comprising:
a server; and
a plurality of portable per-patient devices, each per-patient device being communicably linked to the server over an at least partially wireless link, each per-patient device comprising:
a wireless port for communicating with the server via the at least partially wireless link;
a reader; and
a processor coupled to the wireless port and to the reader, the processor being programmed to:
automatically determine when a first identification transmitter is within a range of the reader;
automatically receive an identification signal transmitted by the first identification transmitter;

send data related to the first identification transmitter, via the wireless port, to the server;

automatically determine when the second identification transmitter that corresponds to the patient ceases to be within the range; and automatically determine when the second identification transmitter that corresponds to the patient is again within the range;

wherein the server is programmed to store information about items that correspond to respective first identification transmitters that are determined to be within the range.

48. A system, as defined in claim 47, wherein the server is programmed to correlate the information about each item with the patient.

49. A system, as defined in claim 48, wherein the processor in each per-patient device is programmed to send data to the server, the data associating the per-patient device with the patient.

50. A system, as defined in claim 47, wherein:
the information about each item comprises data indicative of a time at which the corresponding first identification transmitter was detected;
the processor in each per-patient device is programmed to send information to the server when a previously detected first identification transmitter ceases to be detected within the range; and
the server is programmed to store data indicative of a time at which the previously detected first identification transmitter ceased to be detected.

51. A system, as defined in claim 47, wherein the server is programmed to produce a list of items that correspond to respective first identification transmitters that were detected by a selected per-patient device.

52. A system, as defined in claim 47, wherein the server is programmed to produce a list of items that correspond to respective first identification transmitters that were detected by a per-patient device associated with a selected patient.

53. A system, as defined in claim 47, wherein the server is programmed to produce a list of per-patient devices that detected a selected first identification transmitter.

54. A system, as defined in claim 47, wherein the server is programmed to produce a list of per-patient devices that detected a first identification transmitter that corresponds to a selected item.

55. A system, as defined in claim 47, wherein the server is programmed to produce a list of patients associated with respective per-patient devices that detected a selected first identification transmitter.

56. A system, as defined in claim 47, wherein the server is programmed to produce a list of patients associated with per-patient devices that detected a selected item.

57. A system, as defined in claim 47, wherein the server is programmed to send a message when a previously detected first identification transmitter ceases to be detected.

58. A computer-implemented method for automatically logging items that a patient encounters, each such item having an associated respective first identification transmitter, and the patient having an associated second identification transmitter, the method comprising:
associating an electronic reader with the patient;
listening, with the associated reader, for a signal from a first identification transmitter;
automatically detecting the first identification transmitter when the first identification transmitter is within a range of the reader;

automatically storing, in a computer memory, information about an item that corresponds to the detected first identification transmitter;
automatically determining when the second identification transmitter that corresponds to the patient ceases to be within the range; and
then automatically determining when the second identification transmitter that corresponds to the patient is again within the range.

59. A method, as defined in claim 58, wherein the first identification transmitter comprises a transponder.

60. A method, as defined in claim 58, wherein associating the reader with the patient comprises detecting the second identification transmitter that corresponds to the patient.

61. A method, as defined in claim 58, wherein automatically detecting the first identification transmitter comprises automatically detecting a first identification transmitter that corresponds to a medical device.

62. A method, as defined in claim 58, wherein automatically detecting the first identification transmitter comprises automatically detecting a first identification transmitter that corresponds to an infusion pump.

63. A method, as defined in claim 58, wherein automatically detecting the first identification transmitter comprises automatically detecting a first identification transmitter that corresponds to a ventilator.

64. A method, as defined in claim 58, wherein automatically detecting the first identification transmitter comprises automatically detecting a first identification transmitter that corresponds to a patient monitor.

65. A method, as defined in claim 58, wherein automatically detecting the first identification transmitter comprises automatically detecting a first identification transmitter that corresponds to a drug container.

66. A method, as defined in claim 58, wherein automatically detecting the first identification transmitter comprises automatically detecting a first identification transmitter that corresponds to another patient.

67. A method, as defined in claim 58, wherein automatically detecting the first identification transmitter comprises automatically detecting a first identification transmitter that corresponds to a caregiver.

68. A method, as defined in claim 58, wherein automatically detecting the first identification transmitter comprises automatically detecting a first identification transmitter that corresponds to a fixed structure within a healthcare facility.

69. A method, as defined in claim 58, wherein storing the information about the item comprises storing the information if the detected first identification transmitter is within a predetermined distance.

70. A method, as defined in claim 58, further comprising sending information to a server in response to the first identification transmitter being detected.

71. A method, as defined in claim 58, further comprising sending information to a server in response to a previously detected first identification transmitter ceasing to be detected within the range.

72. A method, as defined in claim 58, wherein listening for the signal from the first identification transmitter comprises continuously transmitting a trigger signal.

73. A method, as defined in claim 58, wherein listening for the signal from the first identification transmitter comprises intermittently transmitting a trigger signal.

74. A method, as defined in claim 58, wherein listening for the signal from the first identification transmitter comprises repetitively transmitting a trigger signal.

75. A method, as defined in claim 58, wherein listening for the signal from the first identification transmitter comprises periodically transmitting a trigger signal.

76. A method, as defined in claim 58, wherein listening for the signal from the first identification transmitter comprises transmitting a trigger signal according to a duty cycle.

77. A method, as defined in claim 58, further comprising producing a list of items that correspond to respective first identification transmitters that were detected by a selected reader.

78. A method, as defined in claim 58, further comprising producing a list of items that correspond to respective first identification transmitters that were detected by a reader associated with a selected patient.

79. A method, as defined in claim 58, further comprising producing a list of readers that detected a selected first identification transmitter.

80. A method, as defined in claim 58, further comprising producing a list of readers that detected a first identification transmitter that corresponds to a selected item.

81. A method, as defined in claim 58, further comprising producing a list of patients associated with respective readers that detected a selected first identification transmitter.

82. A method, as defined in claim 58, further comprising producing a list of patients associated with respective readers that detected a first identification transmitter that corresponds to a selected item.

83. A computer program product, comprising:

a tangible, non-transitory computer-readable medium on which is stored computer instructions for automatically logging items that a patient encounters, each such item having an associated respective first identification transmitter, and the patient having an associated second identification transmitter, which instructions, when executed by a processor, cause the processor to:

automatically determine when a first identification transmitter is within a range of a reader;

automatically receive an identification signal transmitted by the first identification transmitter and store, in a memory, information about an item that corresponds to the first identification transmitter, such that the information is stored beyond end of an encounter between the patient and the item;

automatically determine when the second identification transmitter that corresponds to a patient ceases to be within the range; and automatically determine when the second identification transmitter that corresponds to the patient is again within the range.

* * * * *